US005970977A

United States Patent [19]

Sattelberg

[11] Patent Number: 5,970,977

[45] Date of Patent: Oct. 26, 1999

[54] DEMAND REGULATOR HAVING ADJUSTABLE AIR FLOW

[75] Inventor: Dennis H. Sattelberg, North Tonawanda, N.Y.

[73] Assignee: Harsco Technologies Corporation, Fairmont, Minn.

[21] Appl. No.: 08/950,450

[22] Filed: Oct. 15, 1997

[51] Int. Cl.[6] .......................... A61M 16/00; A62B 9/02; F16K 17/34

[52] U.S. Cl. .............................. 128/205.24; 128/204.26; 137/484.2

[58] Field of Search .................. 137/484.2; 128/205.24, 128/204.26, 204.27

[56] References Cited

U.S. PATENT DOCUMENTS

| | | | |
|---|---|---|---|
| 4,041,977 | 8/1977 | Matsuno | 137/494 |
| 4,140,112 | 2/1979 | Kobzan | 128/204.25 |
| 4,140,113 | 2/1979 | Pedersen | 128/204.26 |
| 4,147,176 | 4/1979 | Christianson | 137/102 |
| 4,214,580 | 7/1980 | Pedersen | 128/204.26 |
| 4,356,820 | 11/1982 | Trinkwalder, Jr. | 128/204.26 |
| 4,616,645 | 10/1986 | Pederson et al. | 128/204.26 |
| 4,796,618 | 1/1989 | Garraffa | 128/204.26 |
| 5,437,268 | 8/1995 | Preece | 128/204.26 |
| 5,701,890 | 12/1997 | Pietrelli | 128/204.26 |

*Primary Examiner*—John G. Weiss
*Assistant Examiner*—Todd Martin
*Attorney, Agent, or Firm*—Eckert Seamans Cherin & Mellot, LLC

[57] ABSTRACT

A demand regulator for self-contained underwater breathing apparatus has a housing and a cover forming a breathing chamber with a mouthpiece. A diaphragm on the chamber is movable with changes in pressure due to user inhalation demand. An inlet valve coupleable to a supply of pressurized air is responsive to the position of the diaphragm. At least one manually adjustable fin can be retracted or positioned across the air flow path through the chamber, for setting the extent of venturi effects tending to displace the diaphragm and open the valve to free flow in the absence of inhalation demand. The venturi adjustment mechanism has a sealed rotatable arm with a radially extending end in sliding engagement with the fin, and preferably the fin has two resilient strips that are spaced apart by a dimple.

18 Claims, 4 Drawing Sheets

DEMAND REGULATOR HAVING ADJUSTABLE AIR FLOW

BACKGROUND OF THE INVENTION

1. Field of the Invention

The invention relates to the regulation of pressurized air in self-contained underwater breathing apparatus, and more particularly to improving the operation of a second stage demand-type regulator by including an adjustable venturi mechanism.

2. Prior Art

Breathing apparatus of the type used in underwater diving systems commonly employ a two-stage regulator arrangement for controlling the flow of air from a pressurized air supply tank. A first stage regulator is mounted directly to the air supply tank and is connected to a second stage regulator by a length of flexible hose. The second stage regulator usually includes a lightweight housing with a mouthpiece capable of being comfortably retained in the user's mouth.

The housing defines a breathing chamber through which the user inhales and exhales air with the aid of a flexible diaphragm in the housing. On a breathing chamber side, the diaphragm communicates with an air inlet valve as well as with the air in the breathing chamber. On the opposite side the diaphragm is exposed to ambient pressure. When the user inhales, the pressure in the breathing chamber falls below ambient pressure. The diaphragm collapses inwardly toward the breathing chamber, opening the air inlet valve and admitting pressurized air into the breathing chamber. When the user exhales, increased pressure in the breathing chamber deflects the diaphragm outwardly relative to the breathing chamber and closes the valve. A check valve arrangement or the like in a wall of the breathing chamber permits air to be exhausted from the housing as the user continues to exhale. The mechanism advantageously is set up so that the user is not required to make an effort to inhale or to exhale that is substantially greater than when breathing in the open air, which effort normally is only minimal.

The opposite may be the case due to the tendency of known regulators to "free flow." Free flow conditions are different than the conditions of normal breathing. Free flowing is caused by the venturi effect, wherein the stream of inhaled air passing through the mouthpiece from the breathing chamber produces a sustained, relatively low pressure in the breathing chamber apart from (or in addition to) the pressure drop caused by any effort exerted by the user to inhale. This low pressure in the breathing chamber affects operation of the diaphragm, i.e., the low pressure keeps the diaphragm collapsed. The inlet valve remains open and continues to admit air into the breathing chamber. Once the flow has begun, the venturi effect can continue the delivery of air after the user's demand to inhale through the demand regulator ceases.

A slight assist from the venturi effect can be desirable because it enhances the inhalation characteristics of the regulator. On the other hand, extended breathing with a regulator that has a considerable tendency to free flow can be annoying. It is also disconcerting for a beginner due to the departure from normal breathing conditions.

Methods and apparatus have been suggested by the prior art for adjusting a demand regulator's tendency to free flow. U.S. Pat. No. 4,041,977—Matsuno; 4,147,176—Christianson; 4,616,645—Pedersen et al.; and 4,796,618—Garraffa, disclose apparatus adapted for regulating the flow of air through a demand regulator. Although providing generally satisfactory operation, many of the prior art demand regulators suffer from inherent problems. In particular, many of the prior art demand regulators do not provide for an easily adjustable air flow so that both the experienced and inexperienced diver may easily and comfortably control venturi related air flow effects according to their preferences and in varying situations.

SUMMARY OF THE INVENTION

According to the arrangements disclosed herein, a demand regulator for use with self-contained underwater breathing apparatus (scuba) comprises a housing and a mating cover assembled to the housing to form an interior recess therebetween. A flexible diaphragm extends across the interior recess to define a breathing chamber. A mouthpiece tube is disposed in fluid communication between the breathing chamber and a breathing port. An inlet valve is connected to a supply of pressurized air, and has at least one orifice for discharging a stream of air into the breathing chamber and in proximity to the breathing port. According to an inventive aspect, at least one fin is disposed in the breathing chamber. Advantageously, a venturi adjustment mechanism in the housing is adjustable from the exterior of the regulator and has a rotatable arm with a portion in sliding engagement with the fin. When the arm is rotated against the fin, the fin moves from a first position wherein substantially all of the fin is in the breathing chamber to a second position wherein a substantial portion of the fin is located in the mouthpiece tube. The arm permits the user to set the position of the fin, and thus the extent of venturi effects, at any position between these extremes.

BRIEF DESCRIPTION OF THE DRAWINGS

These and other aspects of the invention will be appreciated from the following detailed description of preferred embodiments, together with the accompanying drawings, wherein like numbers refer to like parts and further wherein.

DETAILED DESCRIPTION OF THE PREFERRED EMBODIMENT

Figure 1:
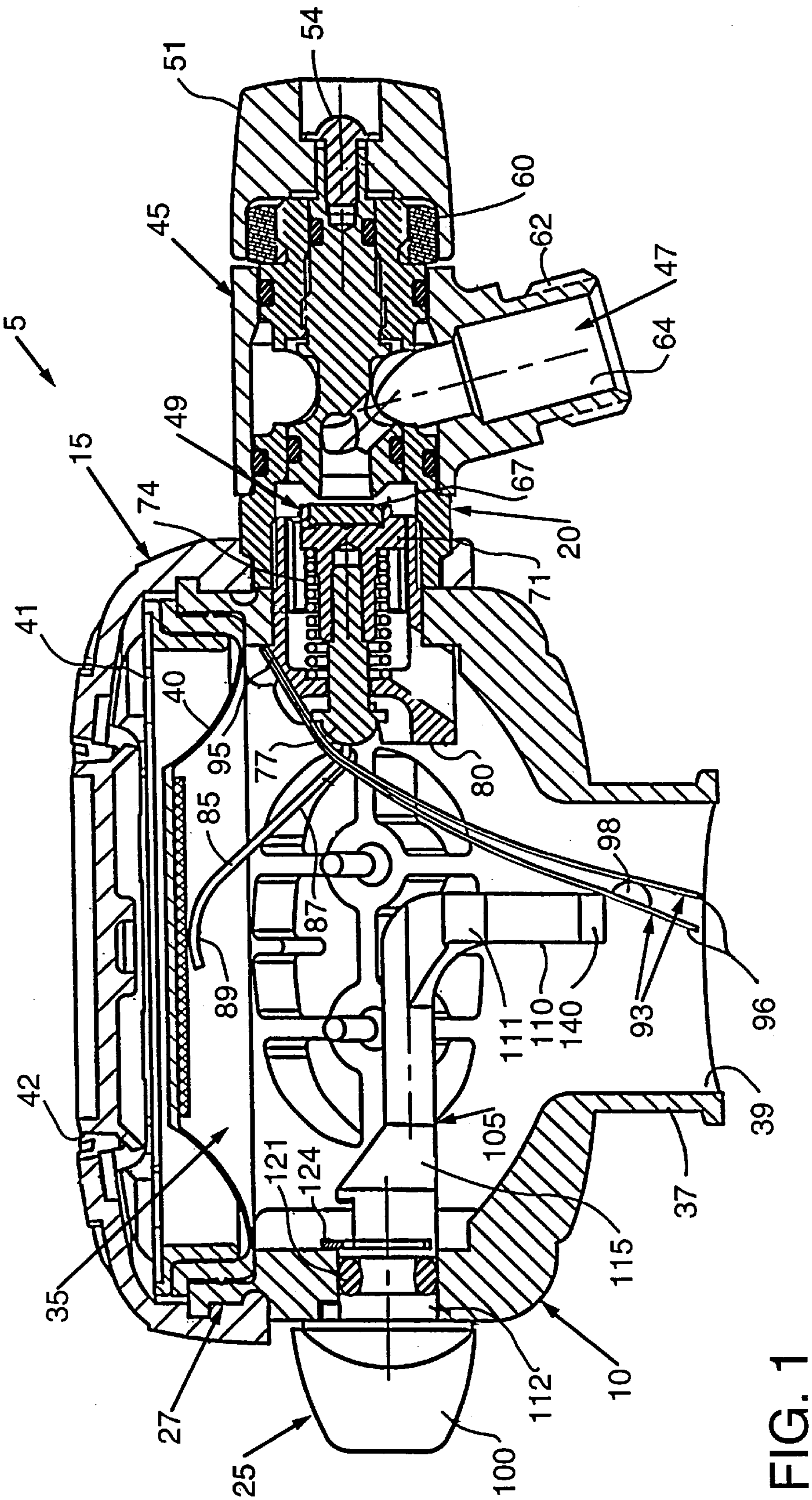
FIG. 1 is a longitudinal cross-section of a demand regulator according to the invention, with the venturi adjustment mechanism in its closed position.

FIG. 1 illustrates a first embodiment of a demand regulator 5 generally comprising a housing 10, a cover 15, an inlet valve assembly 20, and a venturi adjustment mechanism 25. More particularly, housing 10 and cover 15 include corresponding annular interlocking edges 27 that allow housing 10 and cover 15 to be sealingly engaged with one another. A mouthpiece tube 37 projects outwardly from housing 10, and is disposed in fluid communication with breathing chamber 35, via central passageway 39, so as to form a breathing port. Typically, mouthpiece tube 37 has a substantially oval shape.

A flexible diaphragm 40 is sealed across a vented opening, in this case being sealingly fastened to housing 10 by retaining ring 41 so as to form breathing chamber 35 therebetween. When regulator 5 is fully assembled, breathing chamber 35 is closed off by an interference fit of retaining ring 41 against housing 10, which squeezes diaphragm 40 against the housing's inside surface and thereby forms a water tight seal. Mouthpiece tube 37 and inlet valve assembly 20 are the only means of communication with breathing chamber 35. Openings 42 in cover 15 extend between its inner and outer surfaces to vent the outer side of diaphragm 40, exposing that side of diaphragm 40 to ambient pressure. A portion of inlet valve assembly 20 projects into breathing chamber 35 through an aperture provided in the wall of housing 10.

Inlet valve assembly 20 comprises a valve housing 45, an air access port 47, and a valve mechanism 49. Valve housing 45 projects outwardly from a side of housing 10 and provides support and access to valve mechanism 49. Valve mechanism 49 is supported in valve housing 45 and is sealed relative to breathing chamber 35. Valve mechanism 49 is maintained in valve housing 45, via a nut 60, that is sealingly fastened to the end of valve housing 45. An adjustment knob 51 is fastened to valve housing 49 by a screw 54. Adjustment knob 51 allows for variations in the cracking effort exerted by the diver. Air access port 47 includes an external air inlet fitting 62 and a passageway 64. Air inlet fitting 62 is structured to connect to a flexible hose connector so as to provide a path for entry of pressurized air from an external tank (not shown). Passageway 64 extends from an opening in access port 47, through valve housing 45, and communicates with breathing chamber 35 via valve mechanism 49.

Valve mechanism 49 includes a seat 67, a stem 71, a spring 74, a screw 77, and a lever support 80. Seat 67 is disposed at an inner end of passageway 64 and engages the inner open end of passageway 64 when inlet valve assembly 20 is in its normally closed state. Screw 77 extends from breathing chamber 35, through lever support 80, and into a recess in stem 71, where it retains spring 74 in compressed coaxial-relation with stem 71. Stem 71 biases seat 67 toward passageway 64 by means of spring 74. An arm 85 projects into breathing chamber 35 from an inner portion of inlet valve assembly 20. Arm 85 comprises a proximal end 87 and a curved distal end 89. Proximal end 87 is fastened to the portion of screw 77 that is disposed within breathing chamber 35. Curved distal end 89 of arm 85 slidingly engages an inner surface portion of diaphragm 40. In FIG. 1 the diaphragm is shown in a neutral state, namely with the pressure in breathing chamber 35 equal to ambient.

A pair of fins 93 project from one portion of lever support 80, through a portion of breathing chamber 35, and extend into central passageway 39 of mouthpiece tube 37. Fins 93 each comprise elongate strips of thermally conductive material such as copper or the like. Each fin comprises a proximal end 95 fastened to lever support 80 and a distal end 96. A dimple 98 is formed adjacent to distal end 96 of at least one of fins 93, spacing the flat portions of the two fins. Fins 93 are sufficiently wide (see FIGS. 2 and 4) to extend across central passageway 39 of mouthpiece tube 37, and sufficiently long to project into central passageway 39 when deflected by manual operation of venturi adjustment mechanism 25.

Figure 3:
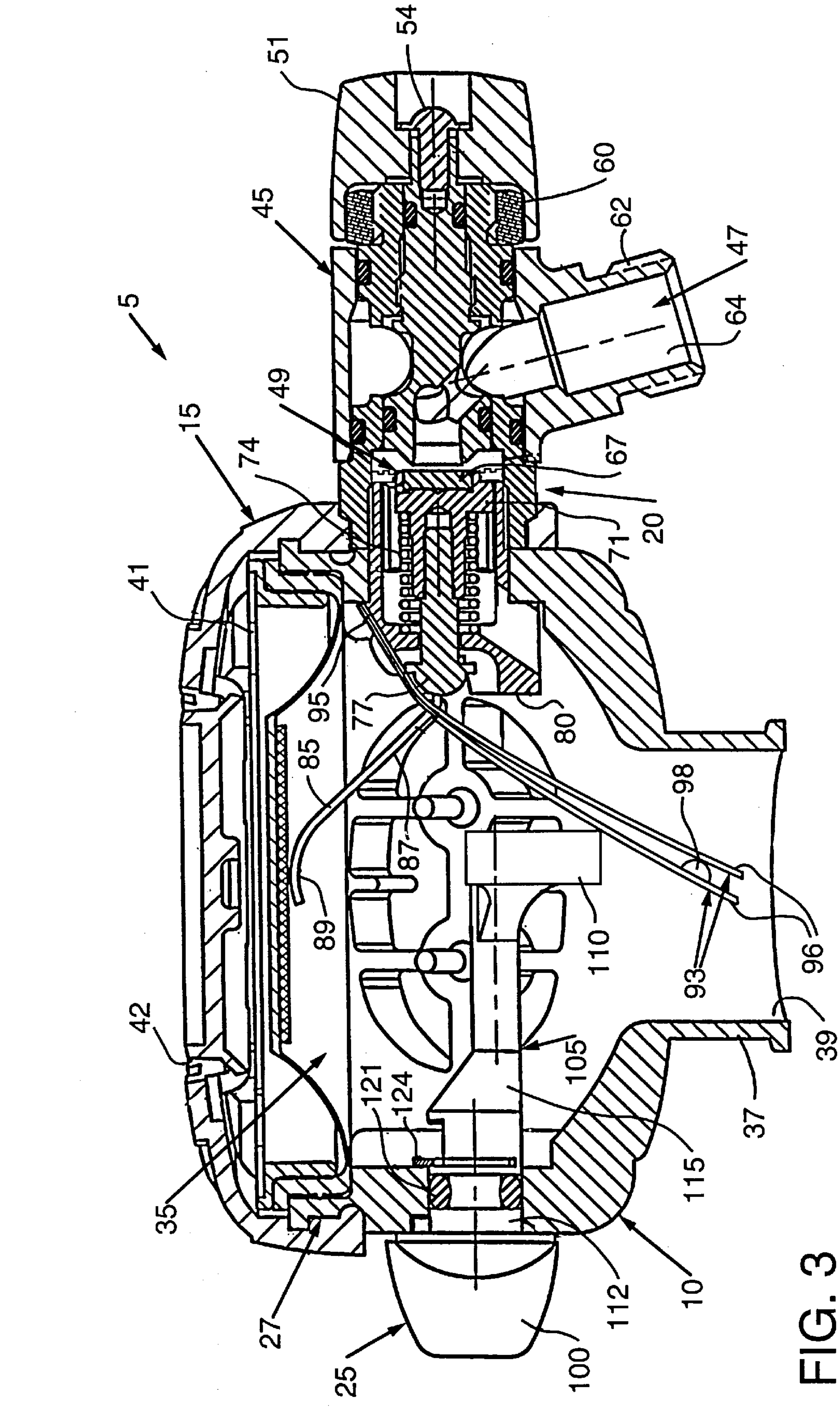
FIG. 3 is a longitudinal cross-section of the demand regulator shown in FIG. 1, but with the venturi adjustment mechanism in its open position; and, FIG. 4 is a transverse cross-section of the regulator shown in FIG. 3.

Venturi adjustment mechanism 25 comprises a handle 100, a shaft 105, and an arm 110. Handle 100 projects outwardly from a side surface of housing 10 and is sized and shaped to be easily manipulated by a diver's fingers. In FIGS. 1 and 3, for example, handle 100 comprises a knob to be gripped between thumb and finger. Shaft 105 projects from an inner side surface of handle 100, through the wall of housing 10, and into breathing chamber 35. A housing wall engaging portion 112 of shaft 105 is sealingly disposed through the wall of housing 10 in such a way that shaft 105 is capable of rotation about its longitudinal axis without allowing for fluid communication between breathing chamber 35 and the ambient environment. The interface between shaft 105 and housing 10 is sealed from the exterior ambient environment by one or more o-rings 121. Shaft 105 is retained in place in the wall housing 10 by a retaining ring 124. Typically, shaft 105 includes a tapered portion 115 to facilitate sliding o-ring 121 into position at a recessed groove formed in housing engaging portion 112. Shaft 105 projects into breathing chamber 35 from the inner surface of housing 10 so as to position arm 110 over fins 93.

Arm 110 projects outwardly in substantially perpendicular relation to the end of shaft 105 that is disposed within breathing chamber 35. Arm 110 may have a bend or jog 111 along its length forming a radial diversion adjustably bearing against fins 93. The length of arm 110 is dimensioned so as to be capable of rotational movement within breathing chamber 35, when shaft 105 is rotated, via handle 100. Shaft 105 may be rotated, for example, by about 90° to 180°. Arm 110 comprises a radiused distal end 140 that allows for clearance of all the internal structures of demand regulator 5 during rotation of shaft 105.

The invention aids in the regulation of free flowing air by allowing the diver manually to adjust the extent of the venturi effect in demand regulator 5. By adjusting the position of fins 93 and the disruption or direction of flow by the fins, venturi adjustment mechanism 25 allows smooth and continuous changes to be made to influence the venturi effect on diaphragm 40. Thus the diver can set the level of free flow experienced during inhaling and/or at the cessation of demand by the diver. A diver may prefer or require the free flow of air to aid breathing. Free flowing of pressurized air helps the diver by reducing the amount of work the diver needs to exert to inflate the diver's lungs with air.

Figure 4:
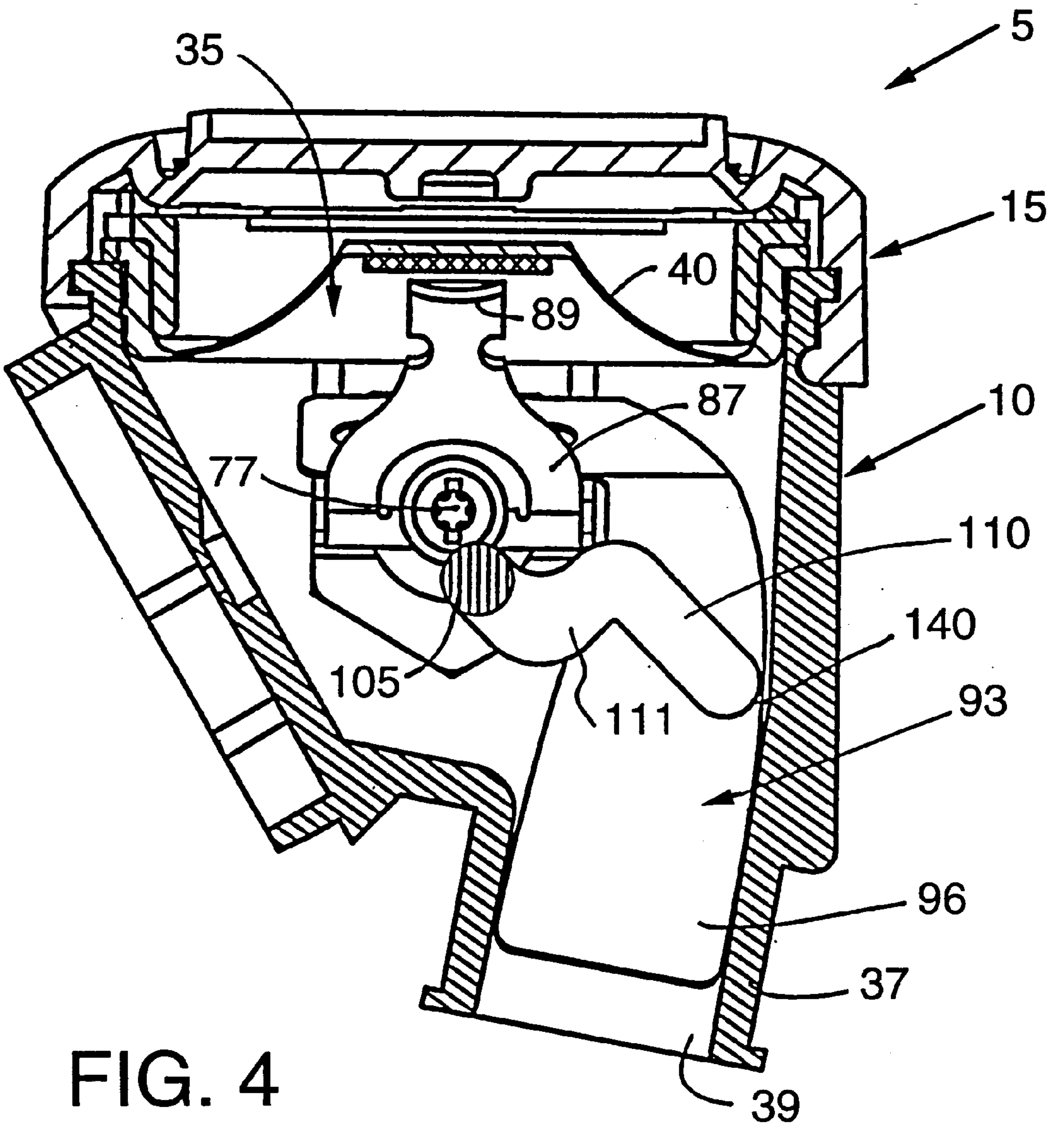

In order to bring on the free flow of air, once breathing has been initiated, the diver actuates venturi adjustment mechanism 25 by rotating handle 100 from a closed position (FIGS. 1 and 2) toward an open position (FIGS. 3 and 4). As this occurs, arm 110 of shaft 105 rotates out of sliding engagement with the outer most surface of outer fin 93. Under the influence of arm 110, fins 93 spring away from the inner surface of central passageway 39. At the same time, the flow of pressurized air from inlet valve assembly 20 is increasingly less confined within the space between the inner surface of fin 93 and the surface of central passageway 39. As the air flow becomes less constricted, conditions are created that are much more favorable to the onset of the well known venturi effect within breathing chamber 35. As a result of this arrangement, the venturi effect within breathing chamber 35 becomes increasingly optimized and free flow initiated, as arm 110 continues to unbias fins 93 and fins 93 move out of central passageway 39.

Figure 2:
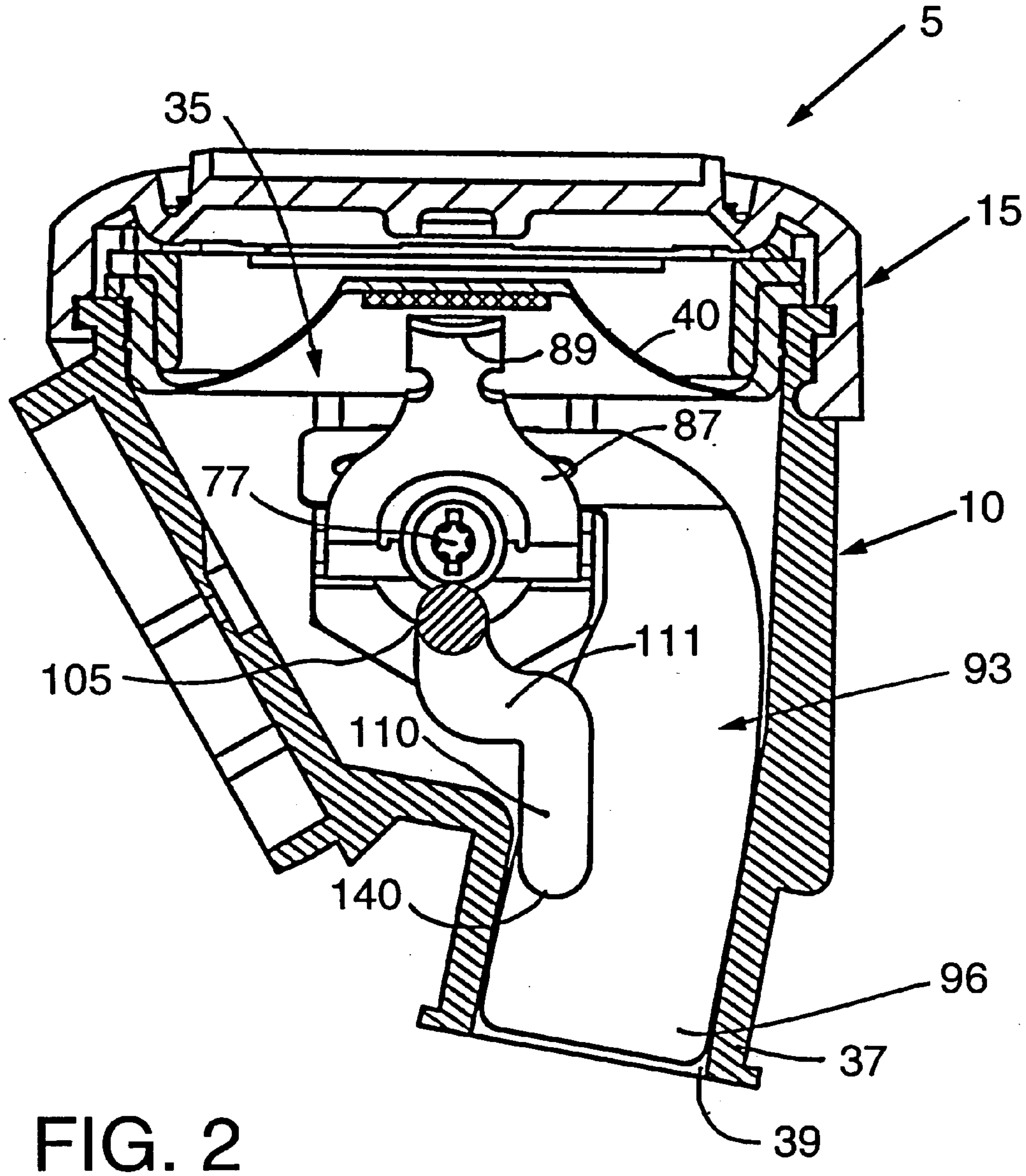
FIG. 2 is a transverse cross-section of the regulator shown in FIG. 1.

When the diver does not wish to free flow air in order to aid breathing, the foregoing procedure is simply reversed. More particularly, handle 100 is rotated from an open position (FIGS. 3 and 4) toward a closed position (FIGS. 1 and 2). This rotation, in turn, causes shaft 105 to rotate moving distal end 140 of arm 110 into sliding engagement with fins 93. As this occurs, distal end 96 of fins 93 moves into central passageway 39. As a result of this repositioning of fins 93, the flow of pressurized air from inlet valve assembly 20, through breathing chamber 35, and into central passageway 39 becomes increasingly constricted. It is this increased constriction of the air flow within breathing chamber 35 and central passageway 39 that diminishes the efficiency of any venturi effect caused by the flow of air through demand regulator 5.

Thus, the positional relationship of fins 93 within breathing chamber 35, under the influence of venturi adjustment mechanism 25, acts to direct and control the flow of pressurized air into mouthpiece tube 37. That is to say, when handle 100 is rotated into a fully opened position (shown in FIGS. 3 and 4) fins 93 are disposed at their outer most position relative to central passageway 39 and free flowing is enhanced by a significant amount. When free flowing is to be reduced, or not desired at all, handle 100 of venturi adjustment mechanism 25 is rotated into a closed position (FIGS. 1 and 2) causing arm 110 to force fins 93 into central passageway 39. This arrangement constricts the flow of pressurized air, discouraging the creation of a venturi.

It is to be understood that the present invention is by no means limited to the precise constructions herein disclosed and shown in the drawings, but also comprises any modifications or equivalents within the scope of the claims.

What is claimed is:

1. A demand regulator for use with a self-contained underwater breathing apparatus, said regulator comprising:

a housing having a housing wall with an inner surface;

a mating cover assembled to said housing to form an interior recess;

a flexible diaphragm extending across said interior recess to define a breathing chamber;

a mouthpiece tube disposed in fluid communication between said breathing chamber and a breathing port;

an inlet valve connected to a supply of pressurized air and having at least one orifice for discharging a stream of air into said breathing chamber and in proximity to said breathing port;

at least one fin projecting into said breathing chamber; and, a venturi adjustment mechanism adjustable from the exterior of said regulator and comprising a rotatable arm having a portion disposed in sliding engagement with said at least one fin such that when said portion of said arm is rotated into sliding engagement with said at least one fin, said at least one fin is biased from a first position wherein substantially all of said at least one fin is located within said breathing chamber to a second position wherein a substantial portion of said at least one fin is located within said mouthpiece tube.

2. Apparatus according to claim 1 wherein said venturi adjustment mechanism comprises a handle, a shaft, and an arm wherein said handle projects outwardly from a side surface of said housing and is sized and shaped so as to be easily manipulated by a diver's fingers.

3. Apparatus according to claim 2 wherein said handle comprises a knob adapted to be gripped between thumb and finger.

4. Apparatus according to claim 2 wherein said shaft projects from an inner side surface of said handle through the wall of said housing and into said breathing chamber.

5. Apparatus according to claim 4 wherein said shaft further comprises a housing wall engaging portion that is sealingly disposed through the wall of said housing such that said shaft is capable of rotation about its longitudinal axis without allowing for fluid communication between said breathing chamber and the ambient environment.

6. Apparatus according to claim 5 further comprising an interface between said shaft and said housing wherein said interface is sealed from the exterior ambient environment by o-rings.

7. Apparatus according to claim 6 wherein said shaft is retained in place in said wall of said housing by a retaining ring.

8. Apparatus according to claim 7 wherein said shaft includes a recessed groove formed in said housing engaging portion and a tapered portion disposed adjacent to said recessed groove for facilitating the sliding application of said o-ring onto said shaft.

9. Apparatus according to claim 8 wherein said shaft projects into said breathing chamber from the inner surface of said housing so as to position said arm over a proximal portion of said at least one fin.

10. Apparatus according to claim 9 wherein said arm projects outwardly in substantially perpendicular relation to said shaft.

11. Apparatus according to claim 10 wherein said arm comprises a bend along its length so as to adjust its engagement with said at least one fin.

12. Apparatus according to claim 11 wherein said arm comprises a length that is dimensioned so as to allow for rotational movement of said arm about said shaft and within said breathing chamber when said shaft is rotated.

13. Apparatus according to claim 12 wherein said shaft is adapted to be rotated about its longitudinal axis by about 90° to 180°.

14. Apparatus according to claim 13 wherein said arm comprises a radiused distal end so as to provide for clearance of all the internal structures of said demand regulator during rotation of said shaft.

15. A demand regulator for a breathing apparatus, comprising:

a housing defining a breathing chamber with a diaphragm and a mouthpiece, the diaphragm being movable as a function of differences between ambient pressure and pressure in the breathing chamber;

an inlet valve coupleable to a supply of pressurized air, the inlet valve being responsive to the diaphragm for permitting air flow from the supply of pressurized air to the mouthpiece when the ambient pressure exceeds the pressure in the breathing chamber;

a venturi adjustment mechanism comprising at least one fin extendable into the housing and a movable arm bearing against said at least one fin, the arm adjustably setting a position of said at least one fin across the air flow for influencing venturi effects on the diaphragm.

16. Apparatus according to claim 15 wherein said venturi adjustment mechanism comprises a rotatable handle, a shaft, and an arm, wherein said handle projects from a surface of the housing for manual adjustment of the position of said at least one fin.

17. Apparatus according to claim 16 wherein said shaft is sealingly extended through a wall of said housing.

18. Apparatus according to claim 15 wherein said arm comprises a radial diversion adjustably bearing against said at least one fin with rotation of the handle.

* * * * *